US00PP09382P

United States Patent [19]

Schumann et al.

[11] Patent Number: Plant 9,382

[45] Date of Patent: Nov. 21, 1995

[54] GERANIUM PLANT NAMED FISMOLI

[75] Inventors: Ingeborg Schumann, Albstadt; Angelika Utecht, Montabaur, both of Germany

[73] Assignee: Florfis AG, Binningen, Switzerland

[21] Appl. No.: 360,647

[22] Filed: Dec. 21, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fismoli, particularly characterized by the combined features of salmon-pink semi-double flowers, numerous flowered umbels on long, strong peduncles, medium green foliage with medium to strong zonation, vigorous growth habit, and early flower response.

1 Drawing Sheet

The present invention comprises a new and distinct cultivar of geranium, botanically known as *Pelargonium peltatum l'Hert,* commonly referred to as ivy geranium, and referred to by the cultivar named Fismoli.

Fismoli is a product of a planned breeding program which had the objective of creating new ivy geranium cultivars with pink flower color, vigorous growth, and good branching ability.

Fismoli was originated from a hybridization made by inventor Ingeborg Schumann in a controlled breeding program in Galdar, Gran Canaria, Spain in 1987. The female parent was a hybrid seedling, identified by number K86/172016, derived from crosses between Salmon Queen and ivy geranium cultivars P3 and P11. Salmon Queen is characterized by large salmon pink flowers, compact growth habit and early flower response. The cultivar P3 has pink double flowers, small leaves with strong zonation and vigorous, loose growth. P11 has single pink-violet flowers, foliage with strong zonation, and vigorous growth. The male parent was an inbred seedling from a hybrid originated by a cross between the red, single flowered cultivar Martine and a mutation from Moulin Rouge having salmon red, semi-double flowers and foliage with weak zonation.

Fismoli was discovered and selected as one flowering plant within the progeny of the stated cross by Ingeborg Schumann in 1988 in a controlled environment in Galdar, Gran Cararia, Spain.

The first act of asexual reproduction of Fismoli was accomplished when vegetative cuttings were taken from the initial selection in autumn 1990 in a controlled environment in Galdar, Gran Canaria, Spain, by, or under the supervision of, Angelika Utecht.

Horticultural examination of plants grown from these cuttings initiated in May 1991, and continuing thereafter, has demonstrated that the combination of characteristics as herein disclosed for Fismoli are firmly fixed and are retained through successive generations of asexual reproduction.

Fismoli has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fismoli, which, in combination, distinguish this geranium as a new and distinct cultivar:

1. Salmon pink semi-double flowers.
2. Medium green leaves with medium to strong zonation.
3. Vigorous growth habit.
4. Early flower response.
5. Floriferous, with numerous flowered umbels on long, strong peduncles.

Of the many commercial cultivars known to the present inventors, the most similar in comparison to Fismoli is Salmon Queen. Reference is made to attached Chart A which compares certain characteristics of Fismoli to those same characteristics of Salmon Queen. In general comparison to Salmon Queen, Fismoli has much more vigorous growth, stronger zonation on leaves, and a more orange tint in flower color.

The accomanying color photographic drawing shows typical flower and foliage characteristics of Fismoli, with colors being as true as possible with illustrations of this type.

In the following description, color references are made to the Royal Horticultural Society Colour Chart. The color values were determined indoors in May from plants grown indoors in Hillscheid, Federal Republic of Germany.

Classification:

*Botanical.*—A hybrid of the species *Pelargonium peltatum l'Hert.*

*Commercial.*—Ivy geranium, cv., Fismoli.

INFLORESCENCE

Umbel:

*Shape.*—Semi-spherical.

*Average diameter.*—100 mm.

*Average depth.*—68 mm.

*Peduncle length.*—200 mm.

*Pedicel length.*—25 mm.

*Pedicel color.*—Green, with slight anthocyanin.

*Number of flowers per umbel.*—15.

Corolla:

*Average diameter.*—50 mm.

*Form.*—Semi-double.

*Number of petals.*—8–10.

*Color (general tonality from a distance of three meters).*—Intense salmon pink.

*Color of upper petals.*—58B-C.

*Color of lower petals.*—58C.

*Markings on upper petals.*—Red veins.

*Color of lower surface of petals.*—52C-D.

*Color of sepals.*—Green.

*Number of sepals.*—6.

Bud:

*Shape.*—Elliptical.

*Color (adaxial).*—Green.

*Color (abaxial).*—Orange.

Reproductive organs:

*Androecium.*—Two (2) fertile anthers, white filaments, yellow-orange pollen.

*Gynoecium.*—5–6 lobed stigma, pink style and stigma.

Spring flowering response period: In Hillscheid, Federal Republic of Germany, in 1993 plants had on average 1.2 flowers opened 15 weeks after planting of unrooted cuttings (pinched plants).

Outdoor flower production: The flower count in 1993 in Hillscheid, Federal Republic of Germany was between 40 and 45 flowers per plant for May through September observation period.

Durability: Shatter resistance good.

Plant

Foliage:

*Form.*—Ivy-shaped with rounded lobes.

*Margin.*—Entire.

*Size of leaf.*—95 mm.

*Color of upper surface.*—Medium green, approximately 137C.

*Color (zonation).*—Brown 166A.

*Tolerance of botrytis.*—Average.

General appearance and form:

*Internode length.*—50–70 mm.

*Branching pattern.*—2.6 branches per week.

*Length.*—105 cm (in September, 35-week-old plants).

CHART A

| CHARACTERISTIC | FISMOLI | SALMON QUEEN |
|---|---|---|
| Flower color | 58B–C | Closest to 58C but has bluish tint |
| Zonation of leaves | Medium to strong | Weak |
| Length of plant | 105 cm | 75 cm |

It is claimed:

1. A new and distinct cultivar of geranium plant named Fismoli, as illustrated and described.

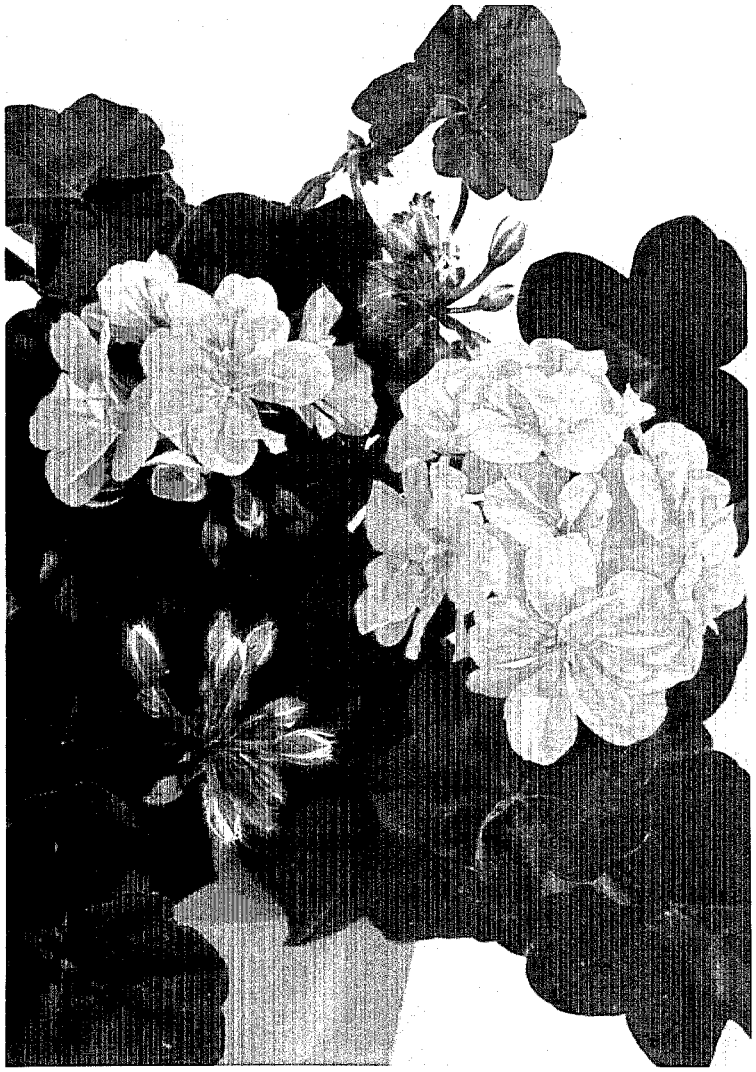

* * * * *